United States Patent [19]

Ohlschlager et al.

[11] 3,954,481
[45] May 4, 1976

[54] LIGHT-SENSITIVE PHOTOGRAPHIC MATERIAL CONTAINING A SUPERSENSITIZED SILVER HALIDE EMULSION LAYER

[75] Inventors: Hans Ohlschlager, Cologne; Oskar Riester, Leverkusen, both of Germany

[73] Assignee: AGFA-Gevaert, A.G., Leverkusen, Germany

[22] Filed: Sept. 24, 1974

[21] Appl. No.: 508,755

[30] Foreign Application Priority Data
Sept. 28, 1973 Germany............................ 2348737

[52] U.S. Cl..................................... 96/122; 96/107; 96/120; 96/123; 96/126; 96/127; 96/130; 96/133; 96/140
[51] Int. Cl.².......................................... G03C 1/08
[58] Field of Search .............. 96/122, 120, 107, 126

[56] References Cited
UNITED STATES PATENTS
3,364,032   1/1968   Jones................................... 96/107
3,458,318   7/1969   Brooks................................. 96/122

*Primary Examiner*—J. Travis Brown
*Attorney, Agent, or Firm*—Connolly and Hutz

[57] ABSTRACT

Sensitization of silver halide emulsions by merocyanines and cationic cyanines and the stability of this sensitization is improved by addition of heterocyclically substituted thioureas of the formula

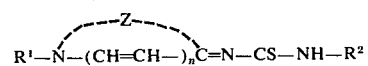

wherein
$R^1$ is alkyl, alkenyl or aryl
$R^2$ is alkyl, cycloalkyl or aryl
$n$ is 0 or 1, and
Z completes a 5- or 6-membered heterocyclic group, preferably one which also contains a sulfur atom.

3 Claims, No Drawings

LIGHT-SENSITIVE PHOTOGRAPHIC MATERIAL CONTAINING A SUPERSENSITIZED SILVER HALIDE EMULSION LAYER

This invention relates to a light-sensitive photographic material containing at least one silver halide emulsion layer which has been sensitized by a cationic cyanine dye or a merocyanine and the sensitivity of which can be increased by the addition of heterocyclically substituted thiourea derivatives.

It is known that the sensitizing action of sensitizing dyes on photographic silver halide emulsions can be considerably increased by certain additives which need not themselves be sensitizing dyes. This effect is known as super-sensitization. The sensitization achieved in this way is, in many cases, extremely sensitive to other necessary additives such as wetting agents, emulsifiers, stabilizers, colour couplers or other, non-sensitizing dyes. This sensitivity to additives is particularly troublesome in colour photographic materials which contain colour couplers or dyes which can be bleached and it manifests itself in insufficient sensitization and a considerable loss in sensitivity on storage under extreme conditions such as elevated temperature or atmospheric moisture. Another disadvantage of conventional supersensitization is that the sensitivity to light is in many cases, increased only in regions of low light intensity so that the gradation is flattened as a whole.

Thus, for example, the supersensitization of cyanine dyes with alkyl or aryl substituted thioureas has been disclosed in U.S. Pat. No. 3,458,318. The supersensitization effects obtained with these compounds, however, are unstable if the material is stored at elevated temperatures and atmospheric humidities, and the method is therefore not in practice usable. It is an object of this invention to provide a permanent increase in the spectral sensitivity of photographic silver halide emulsions and particularly of those which contain colour couplers, and, in addition to achieve adequate gradation without at the same time causing an increase in the tendency of fogging, even under extreme conditions of storage.

It has now been found that the sensitization of silver halide emulsion layers achieved by merocyanines or cationic cyanine dyes can be considerably increased by the addition of heterocyclically substituted thiourea derivatives. The sensitizations achieved with such combinations are found to be completely stable even in the presence of colour couplers and under extreme storage conditions.

This invention therefore relates to a light-sensitive photographic material containing at least one silver halide emulsion layer which has been spectrally sensitized by a merocyanine or a cationic cyanine as hereinafter defined. The material is characterised in that the silver halide emulsion layer in addition contains a heterocyclically substituted thiourea derivative of the following formula

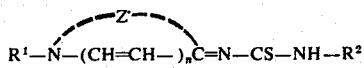

in which
$n = 0$ or $1$,
$R^1$ represents a saturated or unsaturated aliphatic hydrocarbon group preferably containing up to 6 carbon atoms, for example a methyl or ethyl group; or an aryl group, for example a phenyl group;

$R^2$ represents a saturated or unsaturated aliphatic hydrocarbon group preferably containing up to 6 carbon atoms such as a methyl, ethyl, propyl or an allyl group or a substituted alkyl group such as a methoxyalkyl, carbethoxyalkyl or benzyl group; 2. a cycloalkyl group or 3. aryl such as phenyl or naphthyl wich may be substituted, e.g. with alkyl such as methyl, ethyl or trifluoromethyl, phenyl, alkoxy, halogen, carboxyl, carbalkoxy or a group of the formula

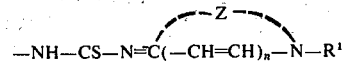

in which $R^1$ and n have the meanings already specified;

Z represents the ring members required to complete a heterocyclic group containing a 5- or 6-membered heterocyclic ring; the heterocyclic group may contain a condensed benzene or naphthalene ring and other substituents; the usual heterocyclic groups of cyanine chemistry are suitable, for example those based on thiazoline including benzothiazoline and naphthothiazoline; those based on selenazoline including benzoselenazoline and naphthoselenazoline; those based on oxazoline including benzoxazoline and naphthoxazoline; those based on imidazoline including benzimidazoline; those based on dihydropyridine including dihydroquinoline and dihydroisoquinoline in which the groups based on 1,2-dihydropyridine are connected to the thiourea group in the 2-position and the groups based on 1,4-dihydropyridine are connected to the thiourea group in the 4-position; those based on thiazolidine, pyrroline, pyrrolidine, hexahydropyridine, thiazoline, triazoline, tetrazoline, oxazolidine, oxadiazoline, dihydropyrimidine, dihydrotriazine, dihydropyrimidone and thiopyrimidone.

The heterocyclic groups may be substituted in any way desired, e.g. with alkyl groups, preferably those containing up to 3 carbon atoms, with aryl such as phenyl, aralkyl such as benzyl, amino, including substituted amino, carbalkoxy, e.g. carbethoxy, carbamyl and sulphamyl including aryl substituted carbamyl and sulphamyl.

Heterocyclically substituted thiourea derivatives in which the heterocyclic group contains sulphur are particularly preferred, i.e. those containing, for example, a thiazoline, thiazolidine, 1,2,4-thiadiazoline or 1,3,4-thiadiazoline ring as the heterocyclic group.

The following are examples of suitable compounds:
Compound No.

1) 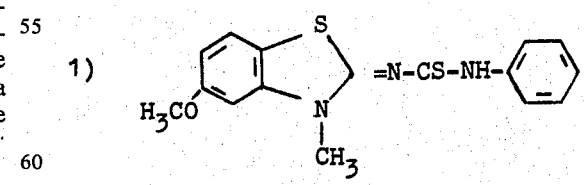

2) 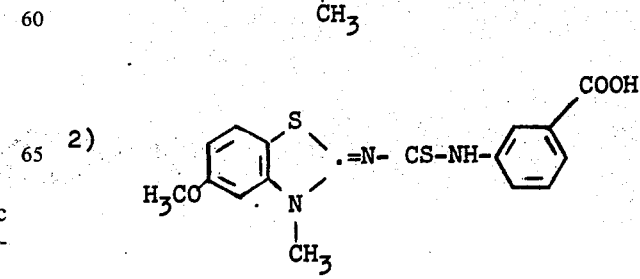

Compound No.
9) 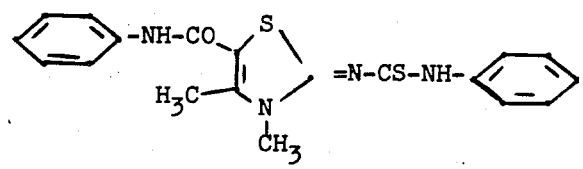
3) 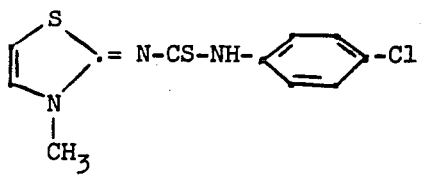
10) 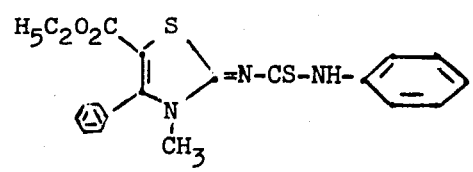
4) 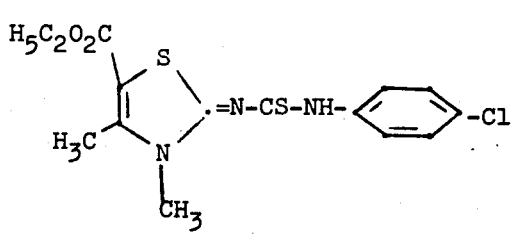
11) 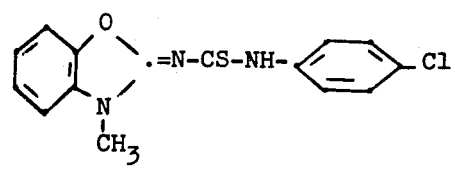
5) 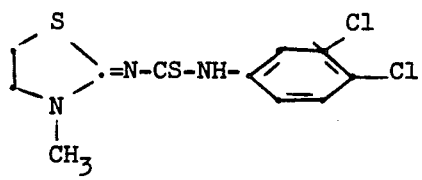
12) 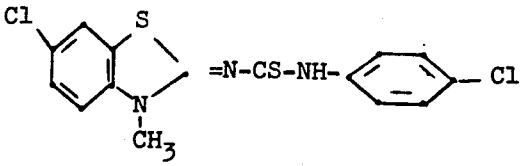
6) 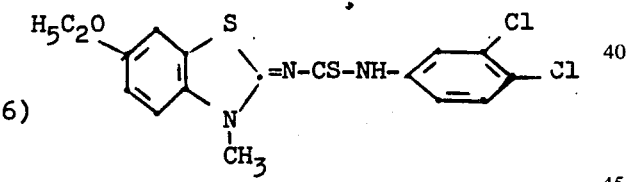
7) 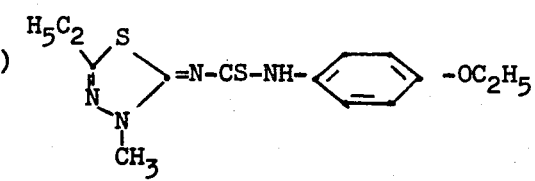
13) 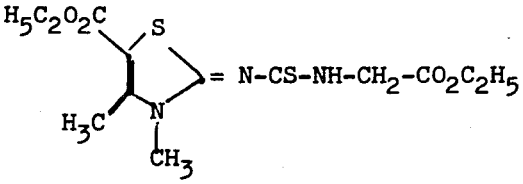
14) 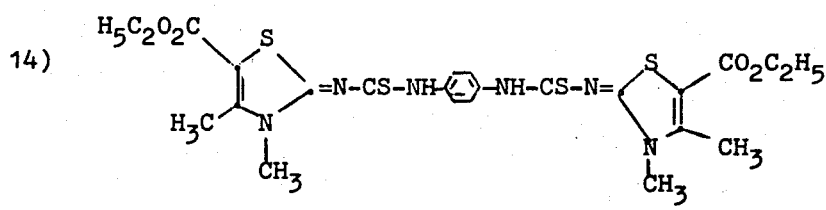
8) 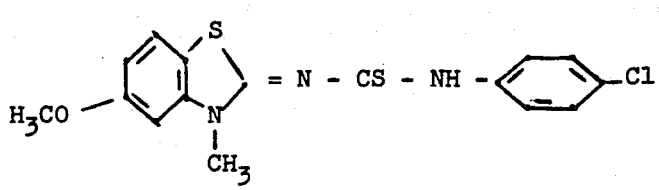

Compound No.
15) 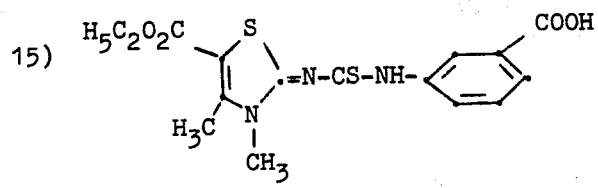
16) 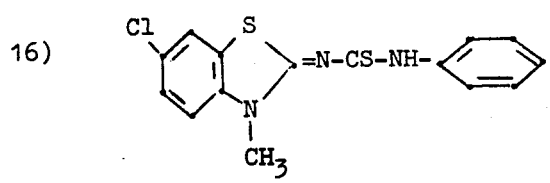
17) 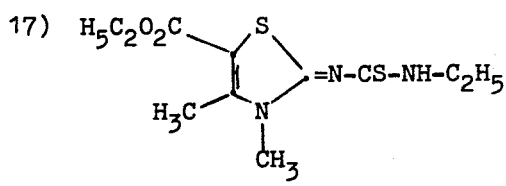
18) 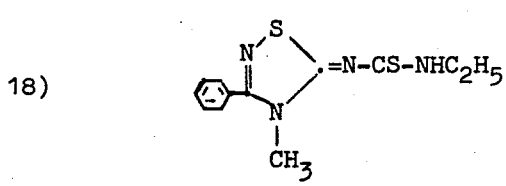
19) 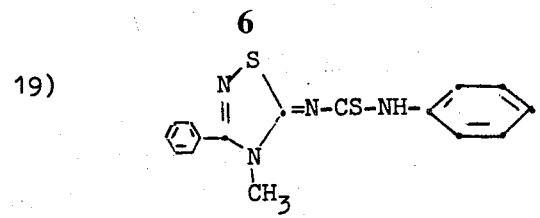
20) 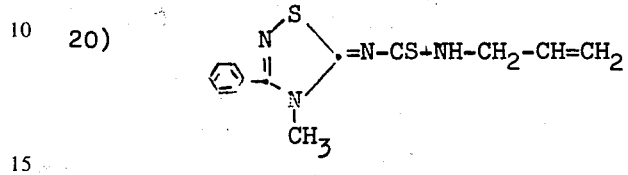
21) 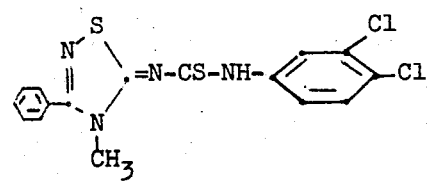
22) 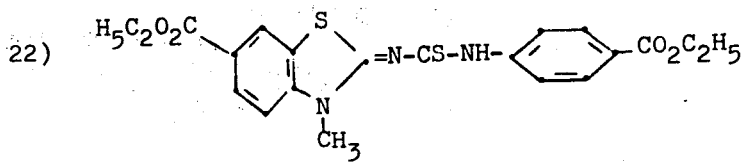
23) 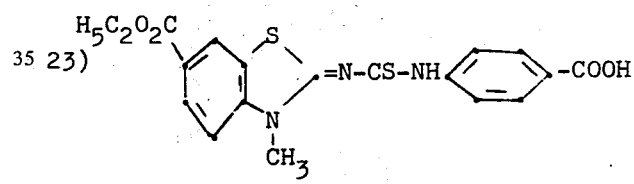
24) 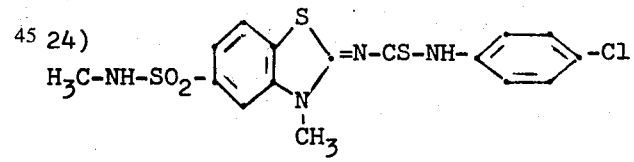
25) 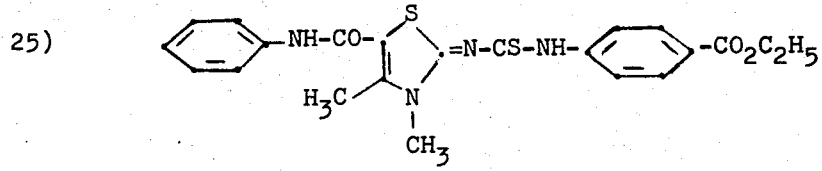
26) 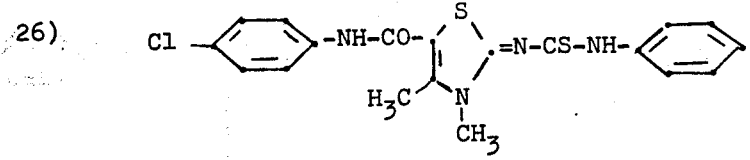

Compound No.
27) 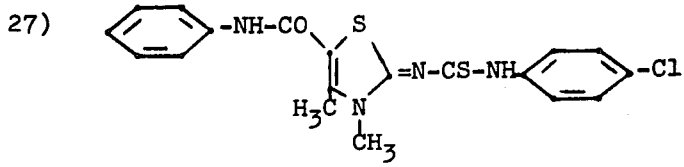
28) 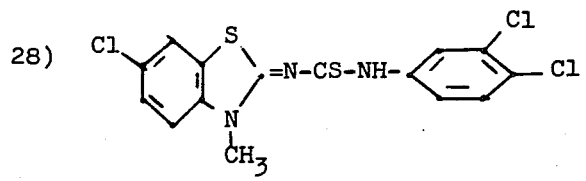
29) 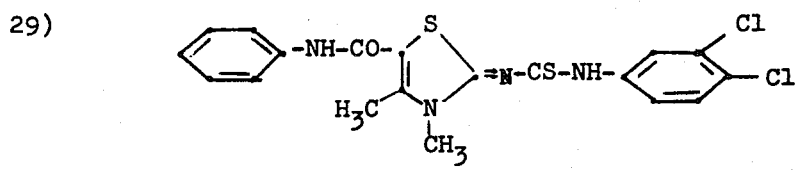
30) 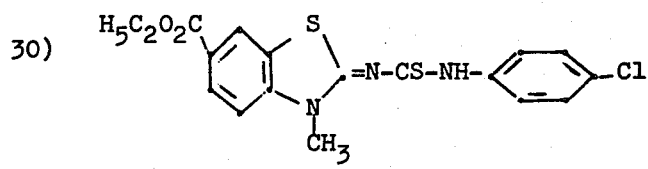
31) 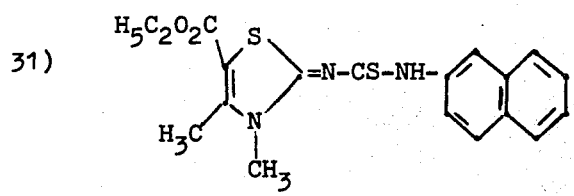
32) 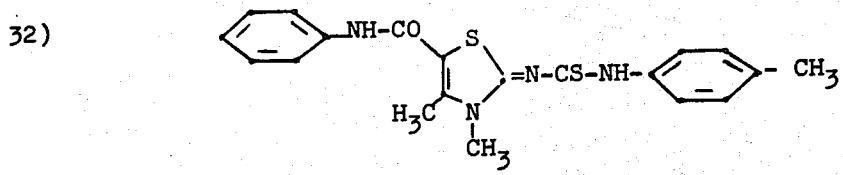
33) 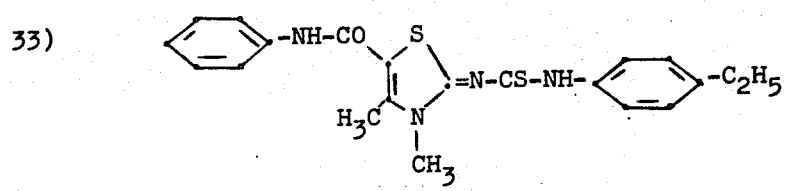

Compound No.
34) 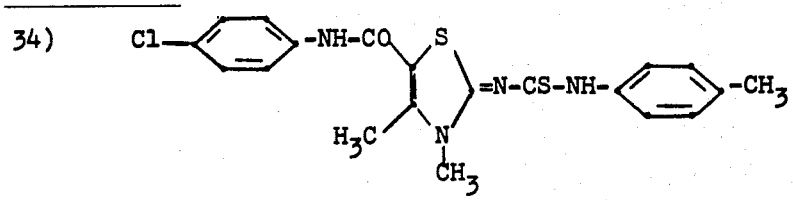
35) 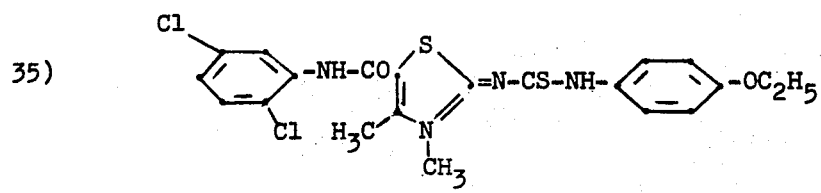
36) 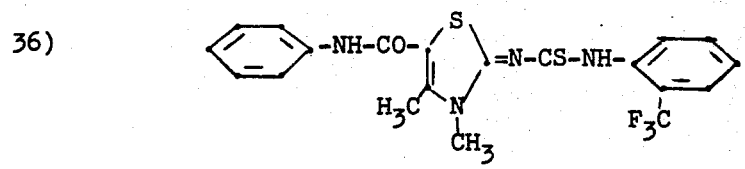
37) 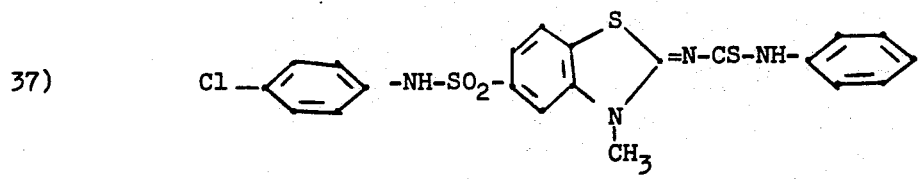
38) 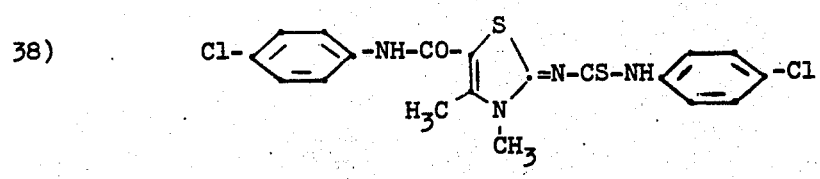
39) 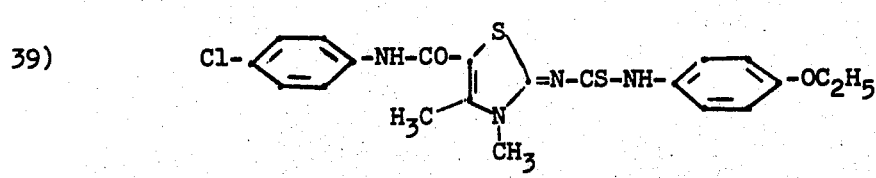
40) 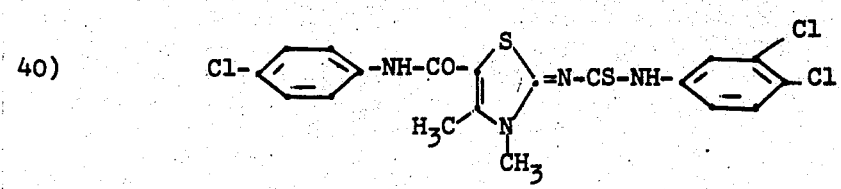
41) 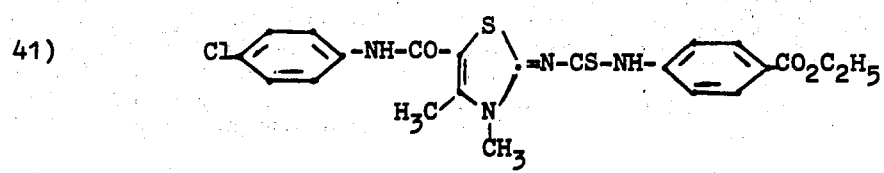

Compound No.

42) 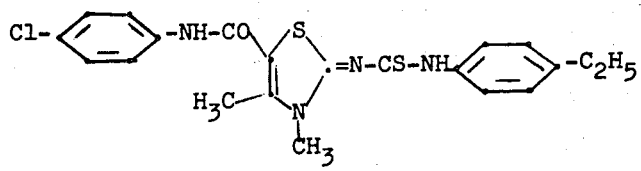

43) 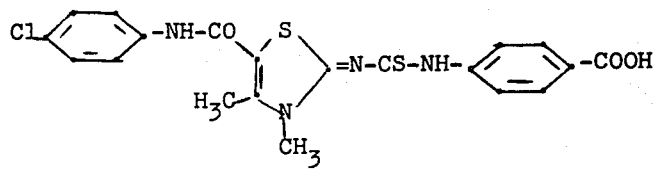

44) 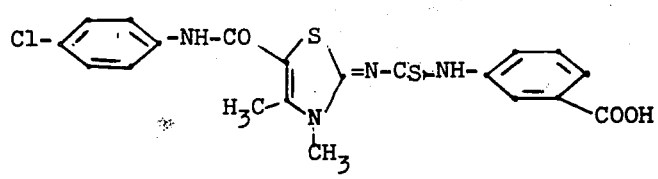

45) 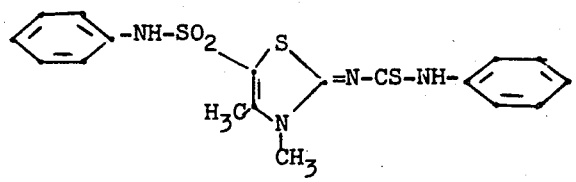

46) 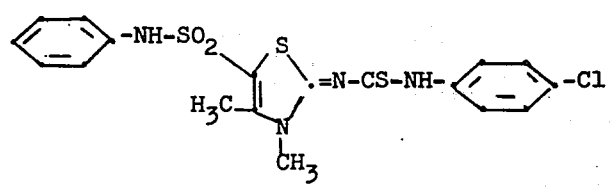

47) 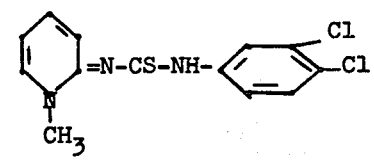

The compounds according to the invention can easily be prepared by the condensation of heterocyclic 2-amino quaternary salts with isothiocyanates without the use of solvents or in an inert solvent with or without the addition of a condensing agent such as piperidine. The preparation of compound 4 is described in detail below. All the other compounds were prepared by the same method.

COMPOUND 4

A solution of 3.5 g of 2-amino-3,4-dimethyl-5-carbethoxythiazolium-p-toluenesulphonate in 10 ml of pyridine and 1.7 g of 4-chlorophenyl-isothiocyanate were heated together under reflux for 30 minutes. The solution was cooled and poured on ice water and the precipitated crude product was suction filtered and recrystallised from chloroform. Yield: 2.9 g, m.p. 229°–230°C.

Merocyanines within the meaning of this application include not only merocyanines proper in which a basic and an acid heterocyclic group are linked together through an even number of methine groups but also those in which the acid heterocyclic group is replaced by an open chain keto methylene compound such as malonitrile or cyanoacetic acid ester (so-called open merocyanines) and those which contain a substituted amino group instead of the basic heterocyclic group (so-called hemioxonoles). Furthermore, the merocyanines proper may be converted into so-called multinuclear merocyanines by quaternization and condensation with an acid heterocyclic group. Cationic cyanine dyes are understood to include all cyanine dyes having two nitrogen atoms connected together by alternating double bonds in a chain of an odd number of methine groups. The methine chain including the two nitrogen atoms has distributed thereon a positive charge and this positive charge is usually shown in the formulae at one of the nitrogens. There is also present a negative charge located on an anion. If the cationic cyanine dye contains by itself anionic groups any external anions may be absent. Thus cationic cyanine dyes include also internal salts or socalled betaines.

The cationic cyanine dyes include the cyanine dyes proper such as mono-, tri-, penta- and heptamethine cyanines, the hemicyanines in which one of the basic heterocyclic groups is replaced by a substituted amino group and the so-called rhodacyanines which are obtained when a merocyanine is quaternized and subsequently reacted with a basic hererocyclic compound.

Examples are given below of dyes whose sensitizing action on silver halide emulsion layers can be enhanced by the heterocyclically substituted thiourea derivatives according to the invention:

Dye

I

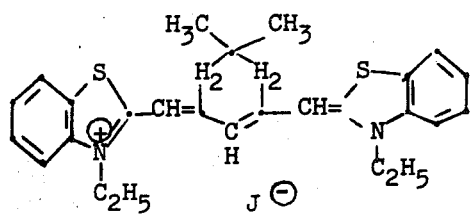

II

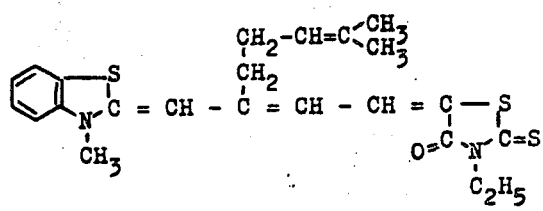

III

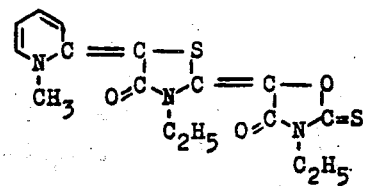

IV

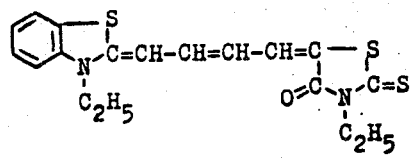

V

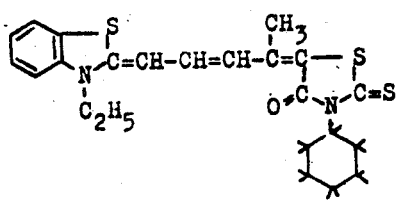

Dye
VI
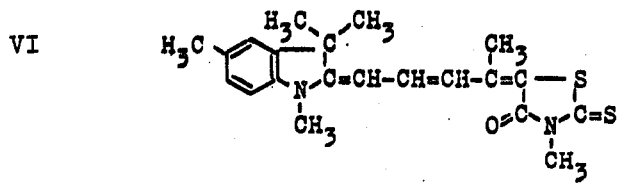
VII
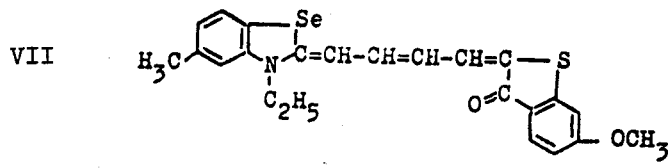
VIII
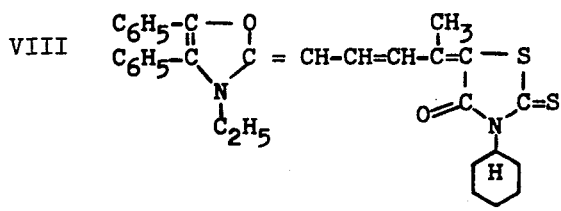
IX
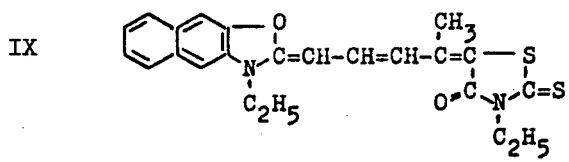
X
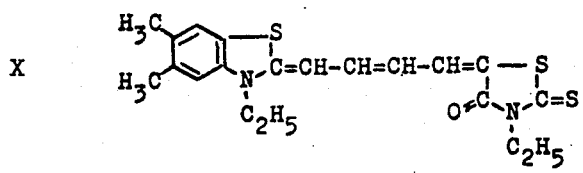
XI
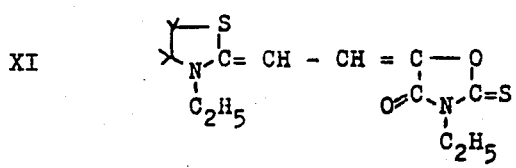
XII
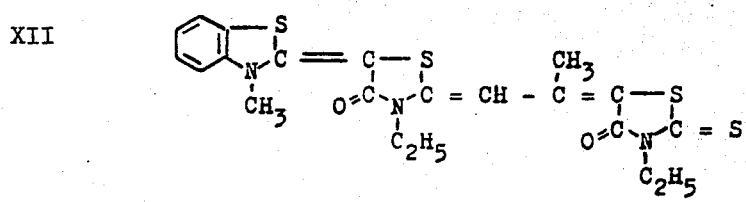

Dye
XIII 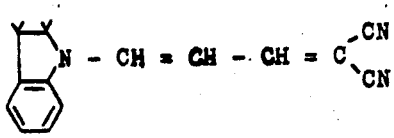
XIV 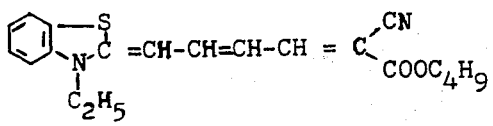
XV 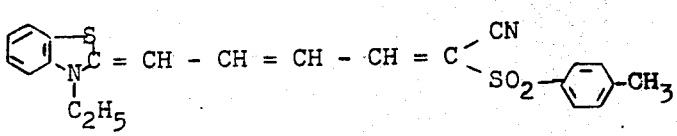
XVI 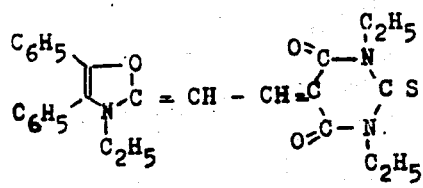
XVII 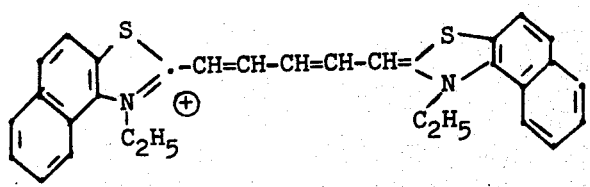
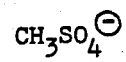
XVIII 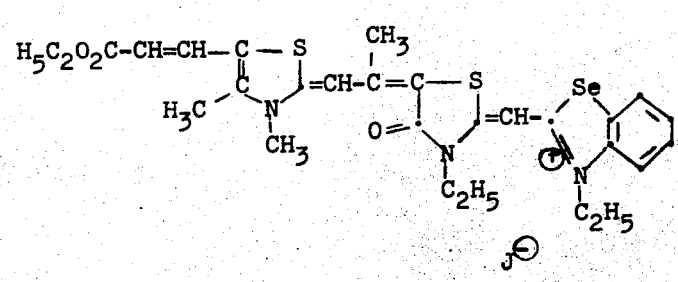
XVIX 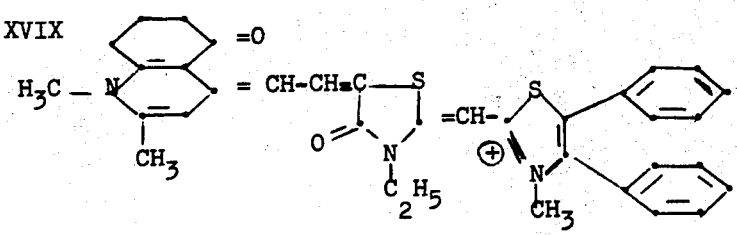

Dye
XX 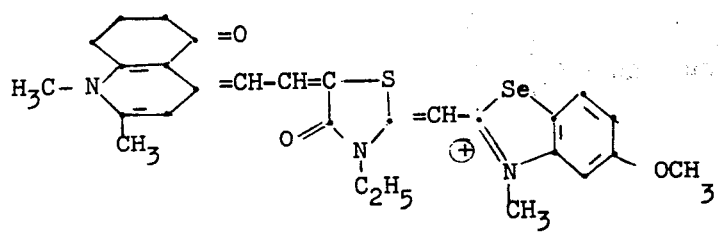
XXI 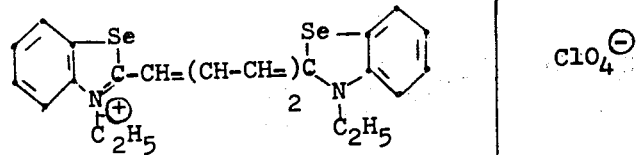
XXII 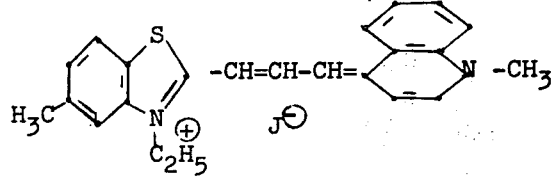
XXIII 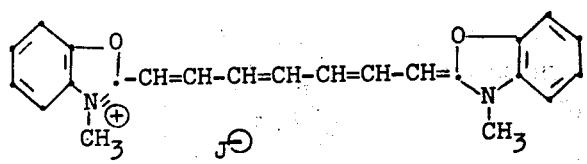
XXIV 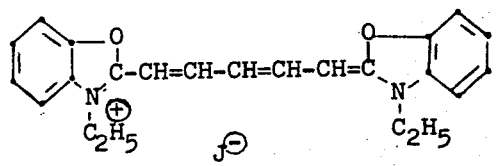
XXV 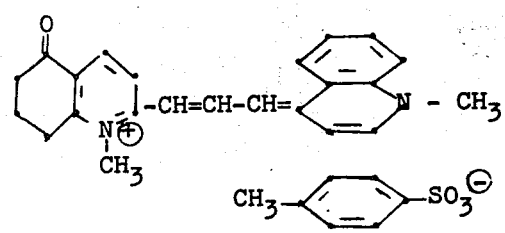
XXVI 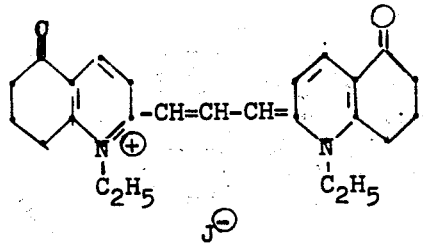

Dye
XXVII 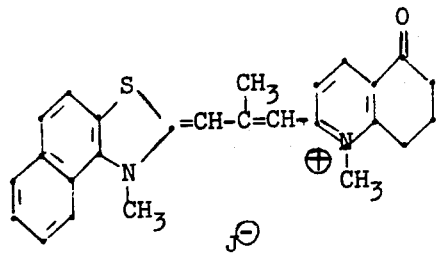
XXVIII 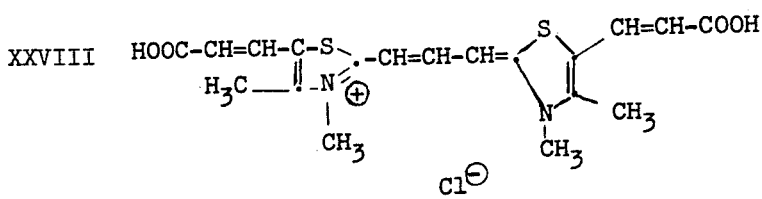
XXVIX 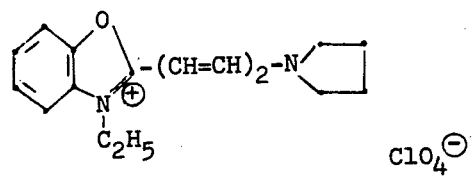
XXX 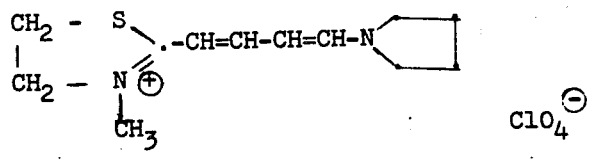
XXXI 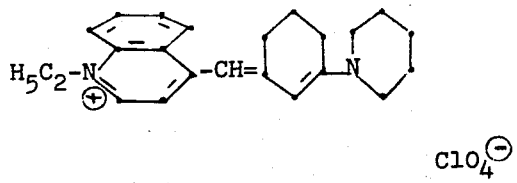
XXXII 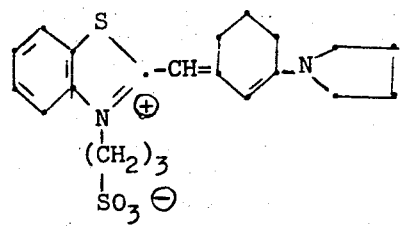

Dye

XXXIII 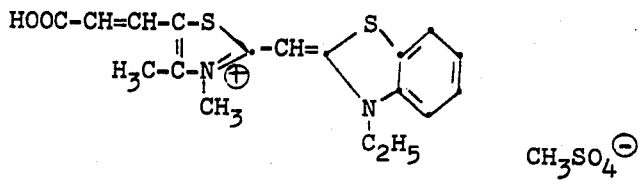 $CH_3SO_4^{\ominus}$

XXXIV 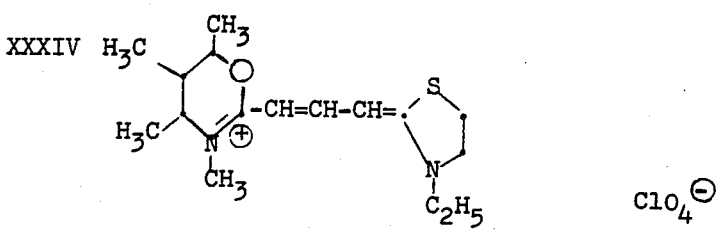 $ClO_4^{\ominus}$

XXXV 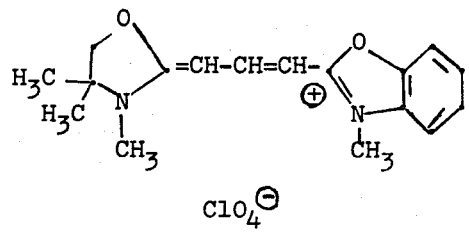

$ClO_4^{\ominus}$

XXXVI 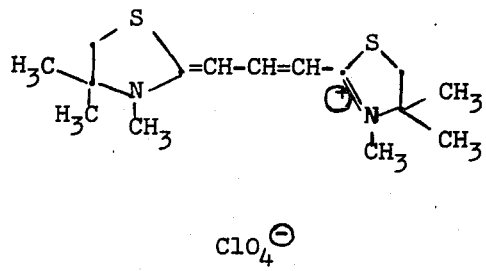

$ClO_4^{\ominus}$

The combinations according to the invention of merocyanines or cationic cyanines and heterocyclically substituted thioureas can be used in any silver halide emulsions. Silver halides may be silver chloride, silver bromide or mixtures thereof which may have a small silver iodide content of up to 10 mols percent.

The silver halides may be dispersed in the usual hydrophilic binders, for example in carboxymethylcellulose, polyvinyl alcohol, polyvinylpyrrolidone, alginic acid or salts, esters or amides thereof or preferably, gelatine.

The heterocyclically substituted thiourea derivatives to be used according to this invention may be added to the silver halide emulsions at any stage of its preparation, for example during precipitation of the silver halide or at some later stage, e.g. before, during or after chemical ripening. The substituted thioureas may be added before, together with or after the sensitizers. The method of addition is generally not critical and depends on the solubility properties of the particular thiourea. The usual solvents also used for the addition of sensitizing dyes may be used, for example alcohols such as methanol or ethanol, acetone, dimethylformamide, pyrrolidone, hydroxypropionitrile, pyridine or phenols, for example cresol. Alternatively, the compounds may be added to the emulsion in the form of aqueous dispersions, e.g. in dilute gelatine solution. They may also be applied to the emulsion by a bathing or immersion process or they may be arranged as an adjacent layer thereby providing contact with the emulsion possibly by means of diffusion into that emulsion. The solvents must, of course, be compatible with gelatine and must not have any deleterious effect on the photographic properties of the emulsion. The quantity of heterocyclically substituted thioureas to be added depends on the sensitizer used and on the strength of the effect desired. Quantities of between 1.5 and $50 \times 10^{-4}$ mol per mol of silver halide are generally suitable, and 5 to $15 \times 10^{-4}$ mol per mol of silver halide are preferred. The quantity of thiourea used is thus approximately of the same order of magnitude as that of the sensitizer. The thiourea is preferably used in from 1 to 20 times the mol quantity of dye. The most suitable concentration of thiourea and of dye can easily be determined for any given emulsion with the aid of the usual routine tests known in photographic practice.

Since the sensitization achieved with the combination according to the invention is substantially unaffected by the presence of colour couplers, it is particularly advantageous to use this sensitization in colour photographic materials which contain colour couplers. This applies to colour couplers of all kinds, e.g. cyan couplers based on phenol or naphthol, magenta couplers based on pyrazolone or indazolone and yellow couplers consisting of open chain ketomethylene compounds. It is unimportant whether the couplers are so-called emulsifying couplers, i.e. hydrophobic couplers, or whether they contain one or more water-solubilizing groups.

The emulsions may also be chemically sensitized, e.g. by adding sulphur compounds such as allylisothiocyanate, allylthiourea, sodium thiosulphate and the like at the chemical ripening stage. Reducing agents may also be used as chemical sensitizers, e.g. the tin compounds described in Belgian Pat. No. 493,464 or 568,687. Polyamines such as diethylenetriamine and aminomethylsulphinic acid derivatives, e.g. according to British patent specification No. 789,823, may also be used.

Noble metals such as gold, platinum palladium, iridium, ruthenium or rhodium and compounds of these metals are also suitable chemical sensitizers. This method of chemical sensitization has been described in the article by R. Koslowsky, Z. Wiss. Phot. 46, 65–72 (1951).

The emulsions may also be sensitized with polyalkylene oxide derivatives, e.g. with polyethylene oxide having a molecular weight of between 1000 and 20,000; condensation products of alkylene oxide and aliphatic alcohols; glycols; cyclic dehydration products of hexitols; alkyl substituted phenols; aliphatic carboxylic acids; aliphatic amines; aliphatic diamines and amides. The condensation products have a molecular weight of at least 700, preferably more than 1000. These sensitizers may, of course, be combined in order to achieve special effects as described in Belgian Pat. No. 537,278 and in British patent specification No. 767,982.

The emulsions may also contain two or more spectral sensitizers, of the type mentioned above, including basic or acid cyanines, hemicyanines, streptocyanines, merocyanines, oxonoles, hemioxonoles, styryl dyes, rhodacyanines and the like. Sensitizers of this kind have been described in the work by F. M. Hamer "The Cyanine Dyes and related Compounds", (1964).

The emulsions according to the invention may contain the usual stabilizers, e.g. homopolar or salt-type compounds of mercury which contain aromatic or heterocyclic rings such as mercaptotriazoles, simple mercury salts, sulphonium mercury double salts and other mercury compounds. Azaindenes are also suitable stabilizers, particularly tetra- or penta-azaindenes, especially those which are substituted with hydroxyl or amino groups. Compounds of this kind have been described in the article by Birr, Z.Wiss.Phot. 47, 2 – 58 (1952). Other suitable stabilizers include e.g. quaternary benzothiazole derivatives, benzotriazoles and the like. Certain heterocyclic mercapto compounds with substituents which have a negative effect have been disclosed in German Auslegeschrift No. 1,447,-577. These act as stabilizers and, at the same time, as supersensitizing additives and they provide particularly good results when used with the combination according to the invention.

The emulsions may also contain white toners such as the known diaminostilbene derivatives as well as so-called shielding or sharpening dyes which are anthraquinone, triphenylmethane or azo dyes. The emulsions may be hardened in the usual manner, for example with formaldehyde or halogenated aldehydes which contain a carboxyl group such as mucobromic acid, diketones, methane sulphonic acid esters, dialdehydes, dimethylourea, dimethylolbenzimidralolone and the like.

The invention will now be explained with the aid of the following examples.

EXAMPLE 1

The silver halide emulsion used contains 19 g of silver per kg, of which 35 mols % is in the form of bromide and 65 mols % as chloride. 10 mg of Dye I dissolved in methanol (1:1000) are added to 1 kg of this emulsion as spectral sensitizer. In addition, 10 g of the sodium salt of 1-hydroxy-4-sulpho-N-octadecyl-2-naphthamide (cyan coupler) is added to the emulsion in the form of 5% aqueous solution. The emulsion is divided into several portions, to each of which are added per kg of emulsion 60 mg of a thiourea according to the invention and indicated in the following table and the different samples are then cast on a bartya paper substrate.

The material is exposed behind a step wedge ($\sqrt[3]{2}$) and an Agfa-Gevaert L 622 red filter (transparent above 622 nm) and developed for 5 minutes at 20°C in a developer of the following composition:

| | |
|---|---|
| Hydroxylamine sulphate | 3 g |
| N-butyl-N-$\omega$-sulphobutyl-p-phenylene diamine | 6 g |
| Potassium carbonate | 87 g |
| Potassium bromide | 1 g |
| Sodium sulphite | 5 g |
| Sodium hexametaphosphate | 2 g |
| made up with water to | 1000 ml. |

The material is then soaked for 1½ minutes and treated with a short stop and fixing bath for 5 minutes. It is then bleach fixed for 5 minutes and finally washed for 10 minutes. In the following table, the sensitivities are expressed as the number of visible steps $\sqrt[3]{2}$ obtained.

Table 1

| Experiment No. | Compound added No. | Sensitivity step $\sqrt[3]{2}$ |
|---|---|---|
| 1 | none | 24 |
| 2 | 1 | 27 |
| 3 | 3 | 28 |
| 4 | 7 | 26 |
| 5 | 10 | 27 |
| 6 | 11 | 27 |
| 7 | 14 | 26 |
| 8 | 17 | 26 |
| 9 | 18 | 28 |
| 10 | 23 | 27 |
| 11 | 24 | 27 |
| 12 | 28 | 27 |
| 13 | 30 | 28 |
| 14 | 32 | 29 |
| 15 | 33 | 29 |
| 16 | 35 | 28 |
| 17 | 36 | 29 |
| 18 | 37 | 28 |
| 19 | 41 | 29 |
| 20 | 46 | 29 |
| 21 | 47 | 27 |

EXAMPLE 2

The same emulsion samples are used as in Example 1 (10 mg of Dye I 10 g of the given cyan coupler). Some samples are treated with 60 mg of the supersensitizer according to the invention per kg and, for comparison, others are treated with 60 mg per kg of the thioureas described in British Pat. No. 1,155,405. The material is processed as in Example 1. The sensitivities obtained are shown in the following Table. This table also shows the values obtained after storage in a heating cupboard and after storage in a tropical cupboard.

In this table, the term "fresh" means that the emulsion was processed only a few hours after it had been cast. "Heat" means that exposure and development were carried out after the samples had been kept at 60°C and 40% relative humidity for three days; "tropical" means that the samples had been kept at 30°C and 80% relative humidity for 3 days before exposure and development.

Table 2

| Experiment No. | Supersensitizer | Sensitivity steps $\sqrt[3]{2}$ | | |
|---|---|---|---|---|
| | | Fresh | Tropical | Heat |
| 1 | none | 24 | 22 | 24 |
| 2 | Comparison I | 26 | 23 | 26 |
| 3 | Comparison II | 24 | 21 | 27 (fog) |
| 4 | Comparison III | 26 | 21 | 27 (fog) |
| 5 | Comparison IV | 25 | 21 | 27 |
| 6 | Comparison V | 26 | 20 | 28 (fog) |
| 7 | 4 | 29 | 30 | 30 |
| 8 | 6 | 27 | 26 | 28 |
| 9 | 12 | 27 | 27 | 28 |
| 10 | 13 | 26 | 27 | 27 |
| 11 | 16 | 27 | 26 | 28 |
| 12 | 20 | 27 | 28 | 29 |
| 13 | 29 | 29 | 29 | 30 |
| 14 | 34 | 29 | 30 | 30 |

The following compounds were used for comparison:
Comparison I: Tetrabenzylthiourea = Compound A of U.S. Pat. No. 3,458,318
Comparison II: N,N'-diethyl-N,N'-diphenylthiourea = Compound B of U.S. Pat. No. 3,458,318
Comparison III: N,N'-dibenzyl-N'-ethyl-N'-phenyl-thiourea = Compound E of U.S. Pat. No. 3,458,318
Comparison IV: N-ethyl-N,N',N'-triphenylthiourea = compound G of U.S. Pat. No. 3,458,318 =
Comparison V: N-methyl-N'-phenylthiourea = Compound I of U.S. Pat. No. 3,458,318

The table clearly shows the superiority of the supersensitizers according to the invention, as regards the sensitivity and stability under conditions of storage in a heating cupboard and a tropical cupboard. Whereas all the samples prepared with supersensitizers according to the invention were free from fog, the samples prepared with the thioureas II, III and V used for comparison showed severe fogging after storage in the heating cupboard.

EXAMPLE 3

To samples of the emulsion from Example 1 containing 10 g of the given cyan coupler are added, per kg, 10 mg of a dye as sensitizer and 60 mg of compound 27 as supersensitizer. The samples are then processed as in Example 1. The following table shows the sensitization maxima (in nm) and the sensitivities obtained with and without supersensitizer (expressed as number of visible steps $\sqrt[3]{2}$).

Table 3

| Experiment No. | Dye No. | Sensitization maximum | Sensitivity Without Compound 27 | $\sqrt[3]{2}$ With Compound 27 |
|---|---|---|---|---|
| 1 | II | 700 | 22 | 26 |
| 2 | IV | 695 | 22 | 27 |
| 3 | V | 680 | 24 | 28 |
| 4 | VI | 690 | 23 | 27 |
| 5 | VIII | 680 | 23 | 27 |
| 6 | X | 690 | 22 | 27 |
| 7 | XVIII | 675 | 27 | 29 |
| 8 | XIX | 665 | 23 | 25 |
| 9 | XX | 675 | 23 | 26 |
| 10 | XXI | 720 | 13 | 21 |
| 11 | XXII | 670 | 21 | 27 |
| 12 | XXIII | 730 | 17 | 27 |
| 13 | XXIV | 625 | 7 | 18 |
| 14 | XXV | 690 | 9 | 19 |
| 15 | XXVI | 650 | 16 | 20 |
| 16 | XXVII | 645 | 5 | 14 |
| 17 | XXVIII | 680 | 16 | 18 |

EXAMPLE 4

10 ml of the following dyes dissolved 1:2000 in acetone, are added to 1 kg of a silver chloride emulsion prepared as described by T.TH. Baker, Photographic Emulsion Technique (American Photographic Publishing Co. Boston/Mass.), 1948, page 217. Table 4 shows the sensitivity values obtained with and without the addition of 60 mg of compound 27 when the emulsion is exposed behind a step wedge ($\sqrt[3]{2}$) and a light yellow filter which absorbs below 435 nm (GG 435 of Agfa-Gevaert AG) and thus eliminates the intrinsic sensitivity of the emulsion.

The material is developed for 2 minutes at 20°C in a developer of the following composition:

| p-Methylaminophenol | 1 g |
| Hydroquinone | 3 g |
| Anhydrous sodium sulphite | 13 g |
| Anhydrous sodium carbonate | 26 g |
| Potassium bromide | 1 g |
| made up with water to | 1000 ml. |

The material is then fixed and washed in the usual manner.

Table 4

| Experiment No. | Dye No. | Sensitization max. | Sensitivity Without Compound 27 | $\sqrt[3]{2}$ With Compound 27 |
|---|---|---|---|---|
| 1 | XIII | 460 | 6 | 14 |
| 2 | XIV | 580 | 20 | 23 |
| 3 | XV | 570 | 18 | 20 |
| 4 | XVI | 495 | 6 | 13 |
| 5 | XXIX | 480 | 8 | 18 |
| 6 | XXX | 460 | 13 | 16 |
| 7 | XXXI | 510 | 13 | 18 |
| 8 | XXXIII | 480 | 7 | 12 |
| 9 | XXXIV | 460 | 7 | 11 |
| 10 | XXXV | 460 | 7 | 12 |
| 11 | XXXVI | 470 | 6 | 13 |

EXAMPLE 5

The following table shows the red sensitivities obtained when increasing quantities of compound 27 are added to a silver chlorobromide emulsion of the kind described in Example 1 which contains 10 mg of dye I as sensitizer and 10 g of the given cyan coupler per kg.

The material was processed in the same way as in Example 1.

Table 5

| Experiment No. | Quantity of Compound 27 (in mg/kg) | Sensitivity $\sqrt[3]{2}$ | | |
|---|---|---|---|---|
| | | Fresh | Tropical | Heat |
| 1 | none | 24 | 22 | 24 |
| 2 | 30 | 28 | 27 | 29 |
| 3 | 60 | 29 | 29 | 30 |
| 4 | 120 | 29 | 29 | 30 |
| 5 | 180 | 28 | 29 | 29 |

We claim:
1. Light sensitive photographic material containing at least one silver halide emulsion layer which has been spectrally sensitized with a merocyanine or a cationic cyanine dye characterised in that the silver halide emulsion layer in addition contains a heterocyclically substituted thiourea derivative of the following formula

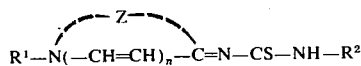

wherein
R$^1$ represents a saturated or unsaturated aliphatic hydrocarbon group containing up to 6 carbon atoms or aryl,
R$^2$ represents
1. a saturated or unsaturated aliphatic hydrocarbon group containing up to 6 carbon atoms,
2. a cycloalkyl group or
3. an aryl group,
Z represents the ring members required to complete a heterocyclic ring selected from the group consisting of a thiazoline group, a thiazolidine group, a 1,2,4-thiadiazoline group and a 1,3,4-thiadiazoline group,
$n = 0$ or 1
said substituted thiourea being present in an effective amount to increase and stabilize the spectral sensitization.

2. Material as claimed in claim 1, wherein Z represents the ring members required to complete a 3,4-dimethyl-5-phenylcarbamyl-thiazoline group.

3. Material as claimed in claim 1, wherein Z represents the ring members required to complete a 3,4-dimethyl-3-phenylsulphamylthiazoline group.

* * * * *